United States Patent
Chen

(10) Patent No.: US 8,070,807 B2
(45) Date of Patent: Dec. 6, 2011

(54) WIRELESS BREACH DETECTION

(75) Inventor: Richard D. Y. Chen, Napa, CA (US)

(73) Assignee: Fulfillium, Inc., Napa, CA (US)

( * ) Notice: Subject to any disclaimer, the term of this patent is extended or adjusted under 35 U.S.C. 154(b) by 1065 days.

(21) Appl. No.: 11/170,274

(22) Filed: Jun. 28, 2005

(65) Prior Publication Data

US 2006/0111777 A1    May 25, 2006

Related U.S. Application Data

(63) Continuation-in-part of application No. 11/122,315, filed on May 3, 2005.

(60) Provisional application No. 60/629,800, filed on Nov. 19, 2004.

(51) Int. Cl.
*A61F 2/12* (2006.01)

(52) U.S. Cl. ............ 623/8; 600/301; 600/372; 600/373; 600/377

(58) Field of Classification Search ........... 623/8, 23.67, 623/7, 23.16; 606/192; 600/301, 372, 373, 600/377, 300; 340/573.1, 539.12; 128/899
See application file for complete search history.

(56) References Cited

U.S. PATENT DOCUMENTS

| | | |
|---|---|---|
| 3,046,988 A | 7/1962 | Moreau et al. |
| 3,055,371 A | 9/1962 | Kulick |
| 3,906,959 A | 9/1975 | Cannon |
| 4,133,315 A | 1/1979 | Berman et al. |
| 4,246,893 A | 1/1981 | Berson |
| 4,416,267 A | 11/1983 | Garren et al. |
| 4,455,691 A * | 6/1984 | Van Aken Redinger et al. . 623/8 |
| 4,485,805 A | 12/1984 | Foster, Jr. |
| 4,501,264 A | 2/1985 | Rockey |
| 4,577,640 A | 3/1986 | Hofmeister |
| 4,607,618 A | 8/1986 | Angelchik |
| 4,648,383 A | 3/1987 | Angelchik |
| 4,694,827 A | 9/1987 | Wiener et al. |
| 4,723,893 A | 2/1988 | Kiyooka et al. |
| 4,739,758 A | 4/1988 | Lai et al. |
| 4,795,463 A * | 1/1989 | Gerow ............................. 623/8 |
| 4,899,747 A | 2/1990 | Garren et al. |
| 4,908,011 A | 3/1990 | Jacobsen et al. |
| 5,081,422 A | 1/1992 | Shih |
| 5,084,061 A | 1/1992 | Gau et al. |

(Continued)

FOREIGN PATENT DOCUMENTS

EP    0103481 A1    3/1984

(Continued)

OTHER PUBLICATIONS

European Search Report and Search Opinion of EP Patent Application No. 05824820.4, mailed Mar. 4, 2010, 11 pages total.

(Continued)

*Primary Examiner* — David Isabella
*Assistant Examiner* — Yashita Sharma
(74) *Attorney, Agent, or Firm* — Wilson Sonsini Goodrich & Rosati

(57) ABSTRACT

Methods and systems for detecting wall breach in inflatable prostheses rely on intrusion of a body fluid or inflation medium to electrically alter a signaling circuit. In one embodiment, an open portion of a circuit is closed to enable or modify a transmitted signal. In another embodiment, electrical current is generated to power an electrical transmission.

10 Claims, 6 Drawing Sheets

U.S. PATENT DOCUMENTS

| | | | |
|---|---|---|---|
| 5,234,454 A | 8/1993 | Bangs | |
| 5,259,399 A | 11/1993 | Brown | |
| 5,476,005 A | 12/1995 | Lindegren | |
| 5,579,765 A | 12/1996 | Cox et al. | |
| 5,833,603 A * | 11/1998 | Kovacs et al. | 600/317 |
| 5,850,144 A * | 12/1998 | Howells et al. | 324/559 |
| 5,993,473 A | 11/1999 | Chan et al. | |
| 6,427,089 B1 | 7/2002 | Knowlton | |
| 6,454,785 B2 | 9/2002 | De Hoyos Garza | |
| 6,579,301 B1 | 6/2003 | Bales et al. | |
| 6,634,216 B1 | 10/2003 | Yasumoto | |
| 6,647,762 B1 | 11/2003 | Roy | |
| 6,656,194 B1 | 12/2003 | Gannoe et al. | |
| 6,733,512 B2 | 5/2004 | McGhan | |
| 6,736,793 B2 | 5/2004 | Meyer et al. | |
| 6,746,460 B2 | 6/2004 | Gannoe et al. | |
| 6,272,914 B1 | 9/2004 | DeLegge | |
| 7,033,373 B2 | 4/2006 | de la Torre et al. | |
| 7,066,945 B2 | 6/2006 | Hashiba et al. | |
| 2001/0001314 A1 * | 5/2001 | Davison et al. | 606/41 |
| 2001/0051766 A1 * | 12/2001 | Gazdzinski | 600/309 |
| 2002/0011934 A1 | 1/2002 | Cacioli et al. | |
| 2002/0055757 A1 * | 5/2002 | Torre et al. | 606/192 |
| 2003/0171768 A1 | 9/2003 | McGhan | |
| 2004/0044357 A1 | 3/2004 | Gannoe et al. | |
| 2004/0059289 A1 | 3/2004 | Garza Alvarez | |
| 2004/0102712 A1 | 5/2004 | Belalcazar et al. | |
| 2004/0106899 A1 | 6/2004 | McMichael et al. | |
| 2004/0122526 A1 | 6/2004 | Imran | |
| 2004/0122527 A1 | 6/2004 | Imran | |
| 2004/0162593 A1 | 8/2004 | Jorgenson et al. | |
| 2004/0162613 A1 | 8/2004 | Roballey | |
| 2004/0186502 A1 | 9/2004 | Sampson et al. | |
| 2004/0186503 A1 | 9/2004 | DeLegge | |
| 2005/0033331 A1 | 2/2005 | Burnett et al. | |
| 2005/0055039 A1 | 3/2005 | Burnett et al. | |
| 2005/0107664 A1 | 5/2005 | Kalloo et al. | |
| 2005/0149186 A1 | 7/2005 | Roballey et al. | |
| 2005/0181977 A1 * | 8/2005 | Hunter et al. | 514/2 |
| 2005/0192614 A1 | 9/2005 | Binmoeller | |
| 2005/0273060 A1 | 12/2005 | Levy et al. | |
| 2005/0275553 A1 | 12/2005 | Weekes | |
| 2006/0004272 A1 * | 1/2006 | Shah et al. | 600/365 |
| 2006/0111632 A1 | 5/2006 | Chen | |
| 2006/0178691 A1 | 8/2006 | Binmoeller | |

FOREIGN PATENT DOCUMENTS

| | | |
|---|---|---|
| EP | 0246999 A1 | 11/1987 |
| EP | 1177763 A | 2/2002 |
| GB | 2090747 A | 7/1982 |
| GB | 2139902 A | 11/1984 |
| GB | 2384993 A | 8/2003 |
| WO | WO 83/02888 A1 | 9/1983 |
| WO | WO 87/00034 A2 | 1/1987 |
| WO | WO 88/00027 A1 | 1/1988 |
| WO | WO 97/33513 A1 | 9/1997 |
| WO | WO 03/095015 A1 | 11/2003 |
| WO | WO 2005/107641 A2 | 11/2005 |

OTHER PUBLICATIONS

Office Action of Japanese Patent Application No. 2007-53307, mailed May 18, 2010, 7 pages total (English Translation Included).

* cited by examiner

WIRELESS BREACH DETECTION

CROSS-REFERENCES TO RELATED APPLICATIONS

The present application is a continuation-in-part of application Ser. No. 11/122,315, filed on May 3, 2005, and claims the benefit under 35 USC §119(e) of prior provisional application No. 60/629,800, filed on Nov. 19, 2004, the full disclosures of which are incorporated herein by reference.

BACKGROUND OF THE INVENTION

1. Field of the Invention

The present invention relates generally to medical apparatus and methods. More particularly, the present invention relates to implantable devices and methods and systems for detecting their failure or impending failure.

All implants of devices, esp. those indicated for long term use, in the human body are highly regulated and must meet certain safety requirements. One such requirement is biocompatibility of the materials used in the construction of the device in the event they come into direct contact with body tissues and fluids. It is known that when a device is implanted in the body, the materials forming the cover and structural elements of the device degrade and fatigue over time. It is also well known that excessive handling during implantation could stress the structural integrity of the device. Failure of the structural integrity of the device or its covering, which eventually happens, causes the contents of the device, which heretofore were confined in the interior of the device, to be in contact with the surrounding tissues and their secretions. Therefore, it would be desirable to detect or to predict such an event before any potentially harmful contents come in contact with the surrounding tissues or before tissue secretions leak into the interior of the device resulting in malfunction.

Prosthetic devices implanted in numerous locations in the body are prevalent in medical practice. Many of these prostheses are designed to assume the structural shape of the body part yet are soft and have similar flexibility to approximate the look and feel of normal human tissue. A common use has been for reconstructing the normal contour, improving the shape, and/or enlarging the size of the human breast. The most common breast prosthesis is a soft elastomeric container made of silicone rubber which is filled or "inflated" with a liquid or gel, typically a saline solution or a silicone gel, or a combination of such filling materials. Typically such prostheses are surgically implanted to fit underneath the skin of the body either between the chest wall and the mammary gland or in place of the mammary gland following a mastectomy. The ideal result after implantation is to achieve the contours and tissue characteristics of a natural breast, and prosthetic devices filled with silicone gel have been found to produce the best cosmetic result. Hence, silicone gel breast implants are the devices of choice in locations where they are approved.

Degradation and fatigue of the silicone rubber container of such breast implants, however, can lead to perforations, tears, ruptures, and seam separations, resulting in the leakage of filling materials to the surrounding tissues. Leakage from a saline filled device is usually harmless as the solution, if uncontaminated, is absorbed. Leakage from the preferred silicone gel filled device is much more problematic. Bleeding of gel at the surface is believed to contribute to the development of capsular contracture, a scarring condition that compresses the implanted device from a soft, natural profile into a rigid, spherical shape. More serious is the migration of leaked silicone gel to other parts of the body such as the lymph nodes and major organs where it becomes unremovable. Consequently, silicone gel has been implicated in many health problems including connective tissue diseases. This risk increases with the length of time the device is implanted.

The problem is exacerbated by the fact that leakage of silicone gel is not easily detected and the rupture of the device cannot be predicted. Unlike saline filled devices where rupture and leakage results in deflation over a short period of time and readily discovered by the patient, silicone gel tends to leak slowly and can go unnoticed for years. Often the rupture is discovered only upon removal of the device for another reason. The only noninvasive method currently sensitive enough to detect such an event reliably is an MRI scan. To monitor the integrity of a silicone gel device by regularly scheduled MRI scans is cost prohibitive. Consequently, the use of silicone gel filled breast prostheses is now highly restricted by regulatory authorities.

Gastric balloons are another type of implantable, inflatable prosthesis which is subject to failure from breach of the wall. Gastric balloons are typically introduced through the esophagus and inflated in situ in order to occupy a significant volume within the stomach. While gastric balloons are typically inflated with saline or other non-toxic materials which are benign if released into the stomach, the balloon structure itself is hazardous if accidentally deflated since it can pass and cause obstruction of the pyloric valve or the intestines distal to the pyloric valve. Any such obstruction is a medical emergency.

For these reasons, it would be desirable to provide apparatus and methods to detect or predict an actual or potential wall breach which can lead to leakage of the filling contents of breast implants, gastric balloons, and the like. Prompt removal of such devices upon leakage or imminent leakage would avert most, if not all, of the ensuing problems. The methods and apparatus will preferably be adaptable for use in any structural design of the device without adversely affecting its structure or, in the case of breast implants, the final cosmetic result, and further be applicable to solid and rigid body implants such as pacemaker and defibrillator canisters. It would be further desirable if the leakage or imminent leakage of the device were detectable to the patient in an easy, rapid, and reliable fashion at home. Additionally, it would be beneficial if the system were able to monitor the device non-invasively on a frequent basis without incurring significant additional cost for each diagnostic event. At least some of these objectives will be met by the inventions described hereinafter.

2. Description of the Background Art

Breast implants and methods for their use are described in U.S. Pat. Nos. 6,755,861; 5,383,929; 4,790,848; 4,773,909; 4,651,717; 4,472,226; and 3,934,274; and in U.S. Publ. Appln. 2003/163197. Gastric balloons and methods for their use in treating obesity are described in U.S. Pat. Nos. 6,746,460; 6,736,793; 6,733,512; 6,656,194; 6,579,301; 6,454,785; 5,993,473; 5,259,399; 5,234,454; 5,084,061; 4,908,011; 4,899,747; 4,739,758; 4,723,893; 4,694,827; 4,648,383; 4,607,618; 4,501,264; 4,485,805; 4,416,267; 4,246,893; 4,133,315; 3,055,371; and 3,046,988 and in the following publications: US 2004/0186503; US 2004/0186502; US 2004/0106899; US 2004/0059289; US 2003/0171768; US 2002/0055757; WO 03/095015; WO88/00027; WO87/00034; WO83/02888; EP 0103481; EP0246999; GB2090747; and GB2139902.

BRIEF SUMMARY OF THE INVENTION

The present invention provides systems and methods for detecting partial or complete breach in the wall of an implantable device, such as an inflatable, implantable prosthesis of the type where a wall at least partially surrounds an inflation medium in one or more inflatable compartments. Other implantable devices subject to wall breach include metal and plastic (polymer) devices which typically comprise rigid-walled housings, such as pacemakers, implantable defibrillators, and the like. These and other devices may contain potentially bioincompatible materials, such as batteries, circuitry, synthetic chemicals, and the like. While the implementation of these systems and methods will be described in detail in connection with breast implants and gastric balloons, it will be appreciated that the principles may be applied to other inflatable prostheses, such as penile implants. The systems of the present invention are incorporated into at least a portion of the wall of the inflatable prosthesis or other device and provide for the emission or transmission of a detectable electronic signal upon breach or partial breach of the wall. As used hereinafter, the term "breach" will refer to any partial or full penetration of the wall structure, or other mechanical disruption which could initiate or lead to the contact of materials inside the wall with tissues or body fluids outside the device.

The signal emission system of the present invention preferably comprises a signaling circuit having one or more components which become exposed to an exterior or interior environment surrounding or within the prosthesis upon breach or partial breach of the wall, wherein such exposure enables, disables, energizes, and/or changes a signal which is emitted by the system. In particular, the wall breach will typically close an open a region within the signaling circuit to cause, enable, disable, or alter the signal emission.

In a first embodiment, the component of the signaling circuit will generate electrical current when exposed to a body fluid and/or the inflation medium by the wall breach. In such cases, the generated electrical current can power an unpowered transmission component to emit the signal. Alternatively, the power can alter a signal which has already been continuously or periodically emitted by the signaling circuit. In the latter case, the signaling circuit may require a separate source of energy, such as a battery or circuit components which are placed on the exterior or interior of the wall so that they are always exposed to fluids to provide for current generation.

Alternatively, the circuit components may include spaced-apart conductors which are electrically coupled to the signaling circuit to "close" the signaling circuit to permit current flow when exposed to a body fluid and/or inflation medium by a wall breach. In the exemplary embodiments described below, the conductors may comprise meshes, films, or other relatively large surface areas covering most or all of the wall so that breach at any point in the wall will provide the intended electrically conductive bridging between the conductors. The coupling of the conductors may also cause, alter, or enable a signal emission to alert the patient of the breach or potential breach. The spaced-apart conductors can have any one of a variety of shapes or configurations, continuous configurations, such as plates and films, or discontinuous configurations, such as lattices, meshes, and the like, can be placed in various locations, preferably near interior portions of the device where body fluids will pool to enhance sensitivity and reliability of the detection.

In a preferred embodiment, the signaling circuit will comprise a passive transponder and antenna which are adapted to be powered and interrogated by an external reader. Such transponder circuitry may conveniently be provided by using common radiofrequency identification (RFID) circuitry where the transponder and tuned antenna are disposed on or within the prosthesis and connected to remaining portions of the signaling circuit. For example, by connecting the transponder circuitry to "open" conductors which may be closed in the presence of body fluids and/or inflation medium, the signal emitted by the transponder upon interrogation by an external reader may be altered. Thus, the patient or medical professional may interrogate the prosthesis and determine whether or not the prosthesis remains intact or a potential breach exists. This is a particularly preferred approach since it allows the user to determine that the transponder circuitry is functional even when a breach has not occurred.

The present invention further provides methods for signaling wall breach of an inflatable prosthesis. Usually, emission comprises closing a signaling circuit when the wall is at least partially breached or generating an electrical current when the wall is at least partially breached. The particular signaling circuits and transmission modes have been described above in connection with the methods of the present invention.

The signaling system of the present invention can be designed to function in a variety of algorithms to notify the patient in a simple, unequivocal fashion. For example, in a toggle algorithm, the transmitter is either on in the static state or preferably off in order to reduce the need for power. Upon direct contact with the body secretions and or device contents, the probes cause the transmitter to turn the signal off or preferably on to be able to send a wireless signal on a continuous basis. The wireless signal or lack thereof is recognized by the detector to notify the patient that the integrity of the device is compromised.

Alternatively, the algorithm could be based on time, amplitude, frequency, or some other parameter. For example, the transmitter may send a wireless signal at a predetermined time interval in its static state. The detector recognizes the length of the interval as normal and the existence of the signal as the system in working order. Upon direct contact with the body secretions or device contents by the probes, the transmitter is enabled to send the same signal at different time intervals or a different signal, which is recognized by the detector to notify the patient that the integrity of the device is compromised. The lack of a signal is recognized by the detector to notify the patient of a detection system malfunction and potential compromise of the integrity of the device.

Optionally, more than one probe or more than one type of probe may be placed internally in different parts or components in the device so that the particular part or component which failed may be identified based on which probe was activated. The transmitter would send different signals for the receiver to display the source of the failure.

The internal probe could be of any shape and is disposed in the interior or preferably in the wall or covering of the device. The preferred configuration is a fine lattice or continuous film of the detection material embedded in the wall or in between layers of the wall covering the entire device, thereby conforming to the shape of the device. Such a configuration optimizes the performance of the system in detecting failures early. As the site of the tear or rupture cannot be predicted, the probe would be unlikely to miss detecting the breach by covering the entire device.

Compromise of the device typically starts with a somewhat linear split or tear in surface of the device wall from mechanical fatigue or handling damage. As the split propagates, it will expose more and more lines of the lattice or area of the film to the body secretions and or device contents. Consequently, as the size and seriousness of the breach increases, the probability of detection increases. Being embedded in the wall of the balloon further enables detection before a full breach of the entire thickness of the device wall.

The detection material could be any metal, polymer, fiber, ingredient, or combination thereof, with or without any coating that can generate an electrical charge or enable flow of electric current when in contact with the body fluids or device contents. For example, an electrical charge could be generated from a non-toxic chemical reaction when the lattice exposed underneath a tear comes in contact with the body secretions. Flow of electric current could be enabled when two ends of an electric circuit hitherto physically separated by electrically non-conductive material in the covering or a structural element of the device are in contact with electrolytes in the body secretions when the electrically non-conductive material is compromised. For example, a charged lattice is embedded in the wall separated by silicone rubber from the ground probe on the external surface of the device. When the lattice is exposed to the electrolytes in the body fluids in the event of a tear, the circuit is closed. Alternatively, the lattice and ground could be separate from each other but interlaced in the wall of the device. Preferred materials include non-corrosive, biocompatible metals and elastomers, inks, or the like which contain electrically conductive particles.

The transmitter can be a simple wireless signal generator triggered by an electric current or preferably a transponder using the well-established RFID technology, i.e., produces a wireless signal when triggered by an interrogating signal. The electric charge generated or the electric current enabled by the probe in contact with the body fluids or device contents enables the transmitter to emit or causes it to emit a wireless signal. Typically, the transponder is powered by the interrogating radio frequency signal so that no power source of its own is required. Alternatively, the transmitter could be powered by a micro battery or by the electrical power generated by a chemical reaction. For protection from degradation by an acidic and electrolyte solution and become potentially toxic, the transmitter or transponder circuit is encased in a highly resistant material, such as silicone rubber or stainless steel. The transmitter or transponder circuit can be placed on the exterior, embedded in the wall, or preferably in the interior of the balloon for shielding from chemical degradation and mechanical stress. It can be placed in any orientation, preferably in the plane where the antenna is most sensitive and the transmitter is most effective in sending and receiving signals through body tissue overlying the device.

The wireless signal from the transmitter is recognized by a detector external to the body. The detector could be simply a receiver tuned to the transmitter's signal or, preferably, a combination of both a transmitter of a signal to interrogate the transponder and a receiver to distinguish the different signals from the transponder. The detector is preferably powered by batteries and portable enough to be worn on a wristband or belt or can be placed conveniently near a place where the patient spends most of his time. Upon receiving a signal that a breach has occurred, the detector will alert the patient to seek medical assistance or alert medical professionals directly through other devices, such as Bluetooth linked to an autodial telephone. The alarm could be auditory, such as beeping sounds, visual, such as flashing LED's or a LCD display, sensory, such as vibrations, or preferably a combination of any or all of the above.

Optionally, the detector could have different auditory, visual, sensory, or different combinations to identify the source of the detected breach, especially with more than one probe or more than one type of probe. For example, LED's of different colors or different sounds could be used. The alarm could further indicate the seriousness of the breach. For example, when multiple probes detect a breach, the volume of the alarm would increase to a higher level.

In the case of non-inflatable implantable devices, such as pacemakers and defibrillators, the devices will be subject to failure due to intrusion of body fluids through breaches, particularly at seams and wire penetrations. Thus, the detector circuit components described above could be located within the device canister near those scams and penetrators at risk of failure so that initial penetration of fluids could be detected before sufficient fluid has entered to cause failure of the device.

DETAILED DESCRIPTION OF THE INVENTION

Figure 1:
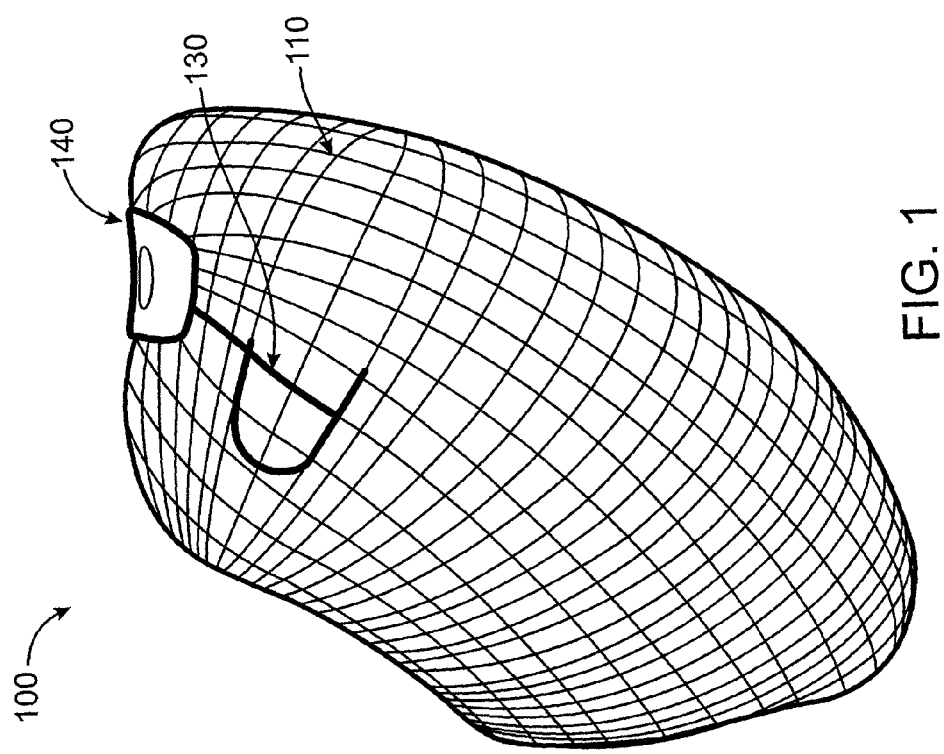
FIG. 1 illustrates a gastric balloon having the wall breach detections system of the present invention incorporated therein.

Referring now to FIG. 1, the gastric balloon 100 includes two electric probes. Probe 130 is on the external surface in contact with the surrounding tissues, body fluids, and contents of the stomach. Probes 130 and 110 can have any of a variety of shapes or configurations, including circular plates, lattices, films, and the like, cover all or a portion of the balloon or other device. Probe 110, shown here in a lattice configuration, provides the second probe incorporated in the wall of the balloon. The probe material could be any metal, polymer, fiber, or combination thereof, with or without any coating that can generate an electrical charge or enable flow of electric current when in contact with the stomach contents. The probes are connected electronically to the wireless transmitter 140, but are separated from each other by at least one layer of non-conductive material in the balloon wall. The transmitter can be a simple wireless signal generator triggered by an electric current or preferably is an unpowered transponder using well-established RFID technology which produces a wireless signal in response to an interrogating signal. In the intact state when the wall is not breached, components 130, 110, and 140 produce an open electrical circuit and the transmitter is inactive, disabled, or enabled to transmit a base signal.

Figure 2:
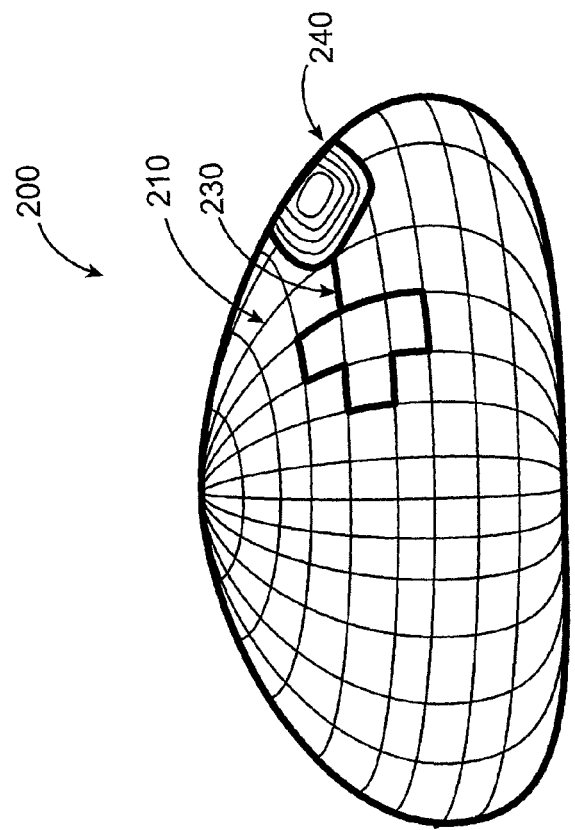
FIG. 2 illustrates a breast implant having the wall breach detection system of the present invention incorporated therein.

Referring now to FIG. 2, a breast implant 200 may be similarly formed with a lattice 210 formed within the breast wall, an external electrically conductive probe 230 formed on or over the exterior surface of the implant, and a transmitter 240 connected to both the lattice and exterior probe. In the case of breast implants filled with low conductivity materials, such as silicone gel, it may be desirable to provide conductive materials to enhance conductivity upon leakage.

Figure 3:
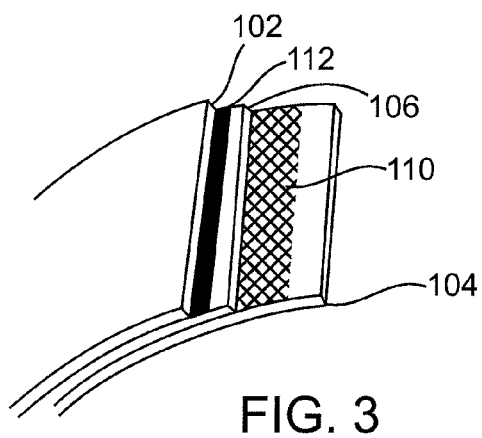
FIG. 3 illustrates a multi-layer wall structure useful for the prostheses of the present invention.

As magnified in FIG. 3, the second internal probe comprises both a fine lattice 110 and a thin film configuration 112 in the wall of the balloon in between, at the minimum two layers, an outermost layer 102 and innermost layer 104. The second internal probe can be also disposed in any enclosed space in the device (not shown). In the configuration described in FIG. 1, probes 130 and 110 and transponder 140 represent one open circuit and probes 130 and 112 and transponder 140 represent a second open circuit. Each open circuit is available to power or enable the transmitter or may enable the transponder to alter a base signal.

After the balloon is deployed in the stomach, the external probe 130 is in contact with the surrounding tissue and body fluids and stomach contents. Upon a breach in the integrity of the wall, such as a tear in the outermost layer 102, the leakage of physiologic fluid or stomach contents with electrolytes into the tear forms a salt bridge that closes the circuit formed probes 130 and 112 and transponder 140. Once the circuit is closed, a toggle is switched in the transponder, which will be enabled to transmit a "layer 102 breach" signal. Tears through layer 106 in the balloon wall will allow leakage of physiologic fluid or stomach contents with electrolytes into the tear forming a salt bridge that closes the circuit formed probes 130 and 110 and transmitter 140. Closing this circuit switches another toggle in the transponder, which will be enabled to transmit a "layer 106 breach" signal.

Figure 4:
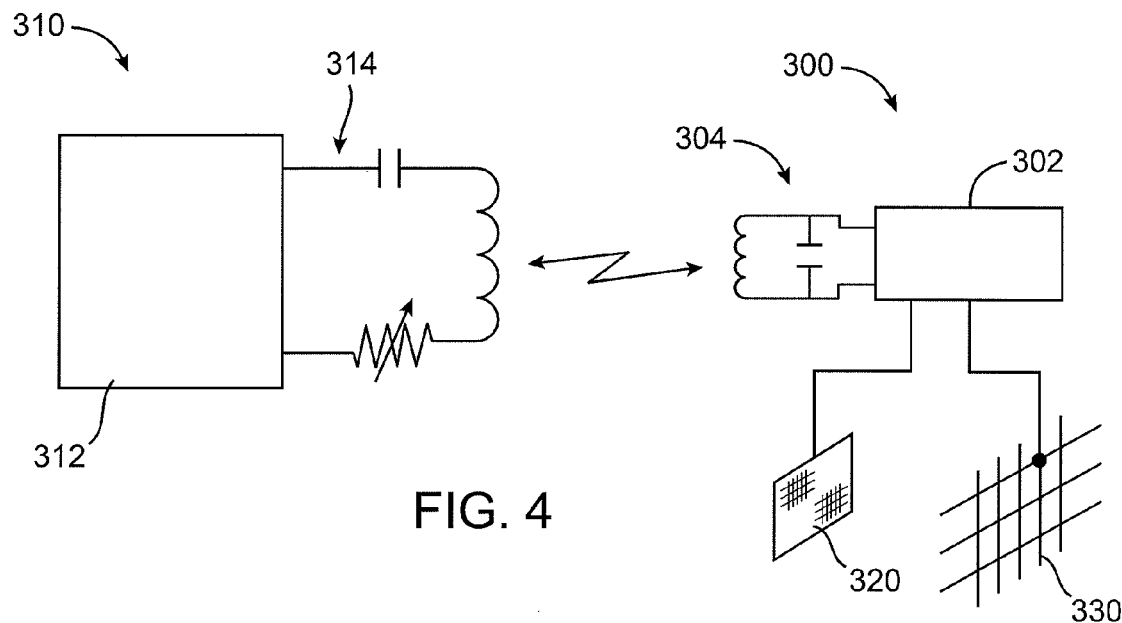
FIG. 4 illustrates a passive transponder system which may be utilized in the wall breach detection systems of the present invention.

The preferred radiofrequency identification circuit is shown schematically in FIG. 4. The circuit comprises a transmitter component 300 which includes transponder circuitry 302, typically formed as an integrated circuit, and a tuned antenna-capacitor circuit 304. A reader 310 comprises circuitry 312 including the power supply (typically a battery) demodulator circuitry, decoder circuitry, and the like. An antenna 314 is tuned so that it can communicate wirelessly with the antenna 304 of the transponder 300. Operation of this circuitry is generally conventional and provides for energizing, demodulating, and decoding signals between the external and implanted components. The transponder circuitry, however, will be modified so that the conductive elements implanted in the wall, such as film 320 and lattice 330 may enable or alter the signal emitted by the transponder when the conductive elements are bridged by body fluids or inflation medium. In the preferred embodiments described above, electrical coupling of the conductors 320 and 330 will alter the signal that is produced by the transponder 302. In that way, the patient or other user will be able to interrogate the transponder and receive a base or "normal" response signal when no wall breach has occurred. In the event of a wall breach, the signal emitted by the transponder will be altered so that the breach will be known to the user.

Figure 5:
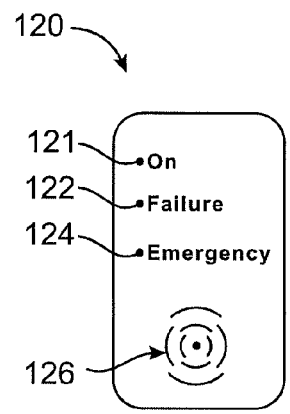
FIG. 5 illustrates a hand-held interrogation unit useful with the systems of the present invention.
Figure 6A:
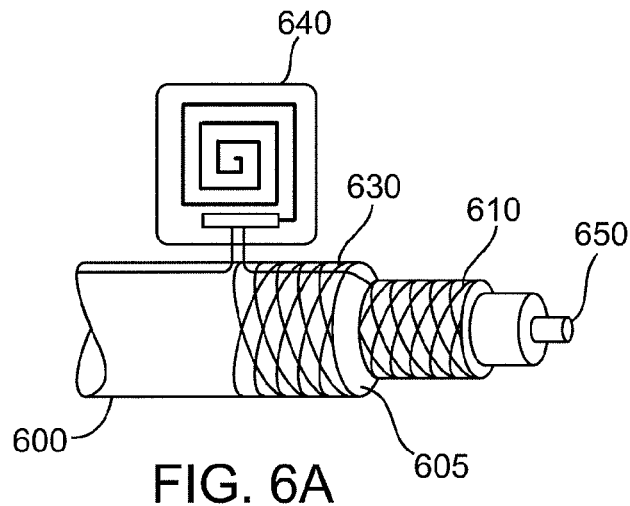
Figure 6B:
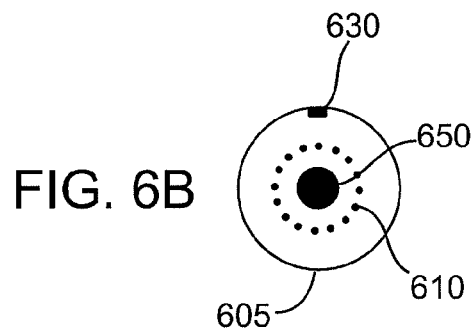
Figure 6C:
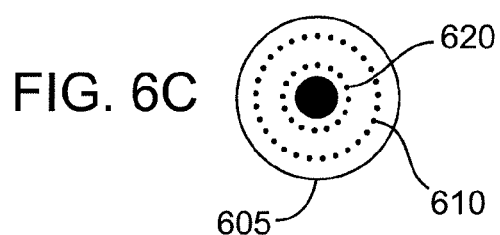
Figure 6D:
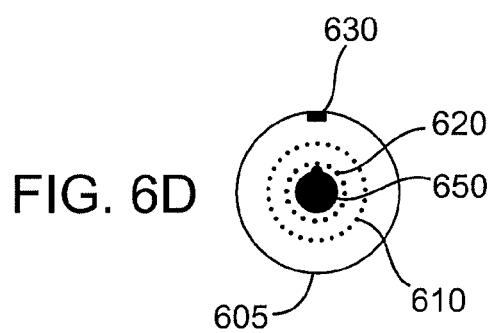
Figure 6E:
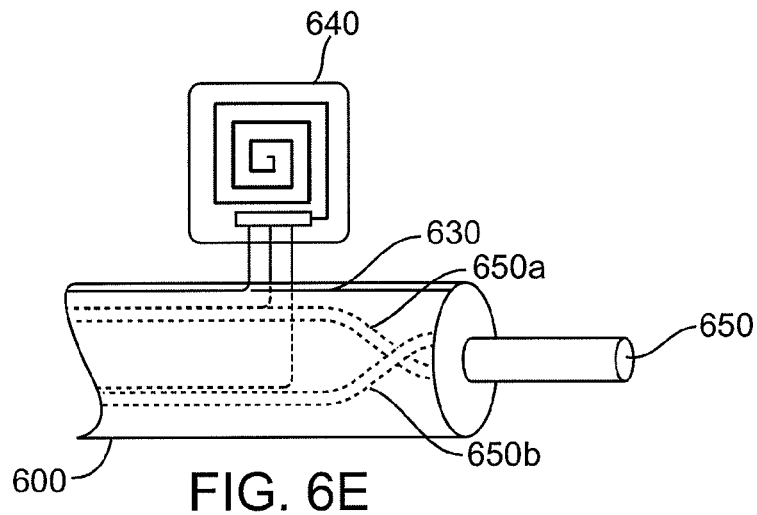
Figure 6F:
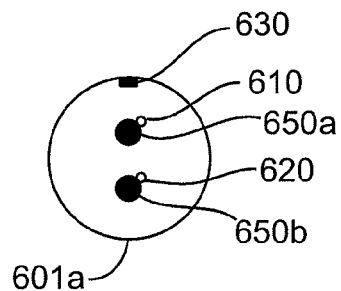
Figure 6G:
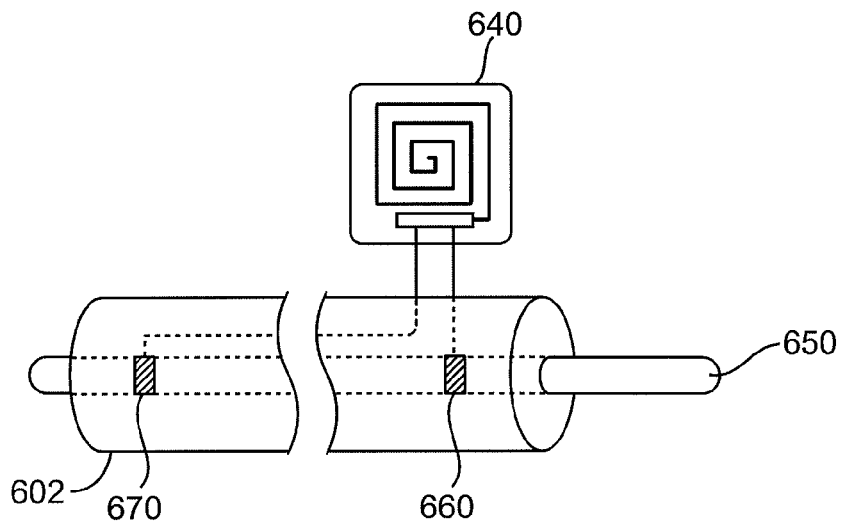
Figure 6H:
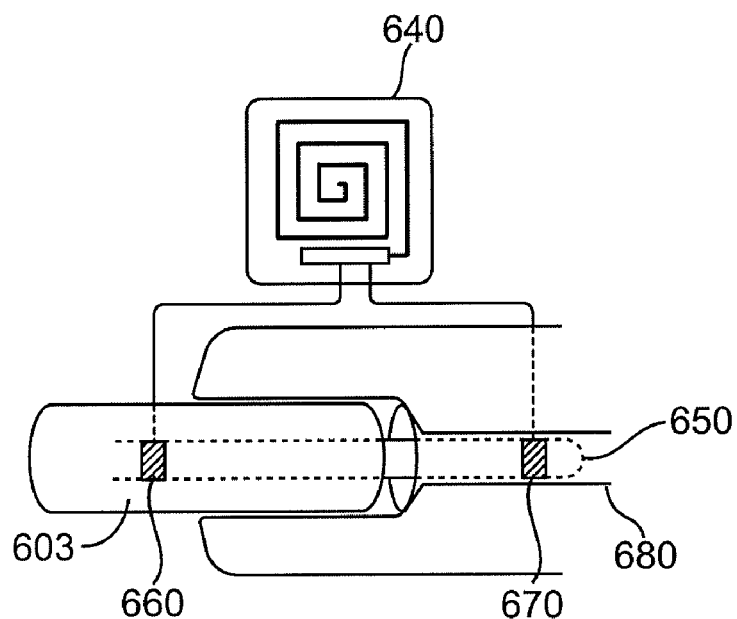
Figure 6I:
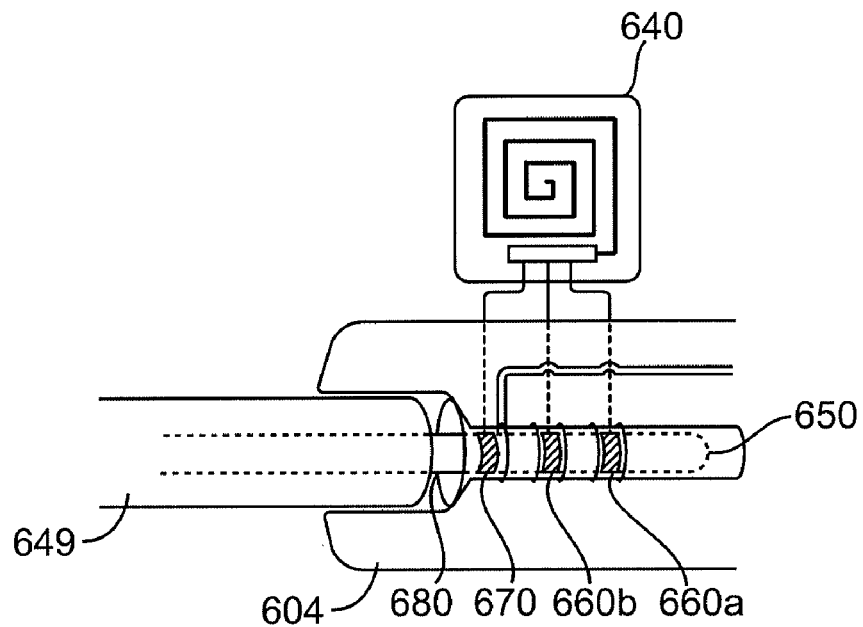
Figure 7:
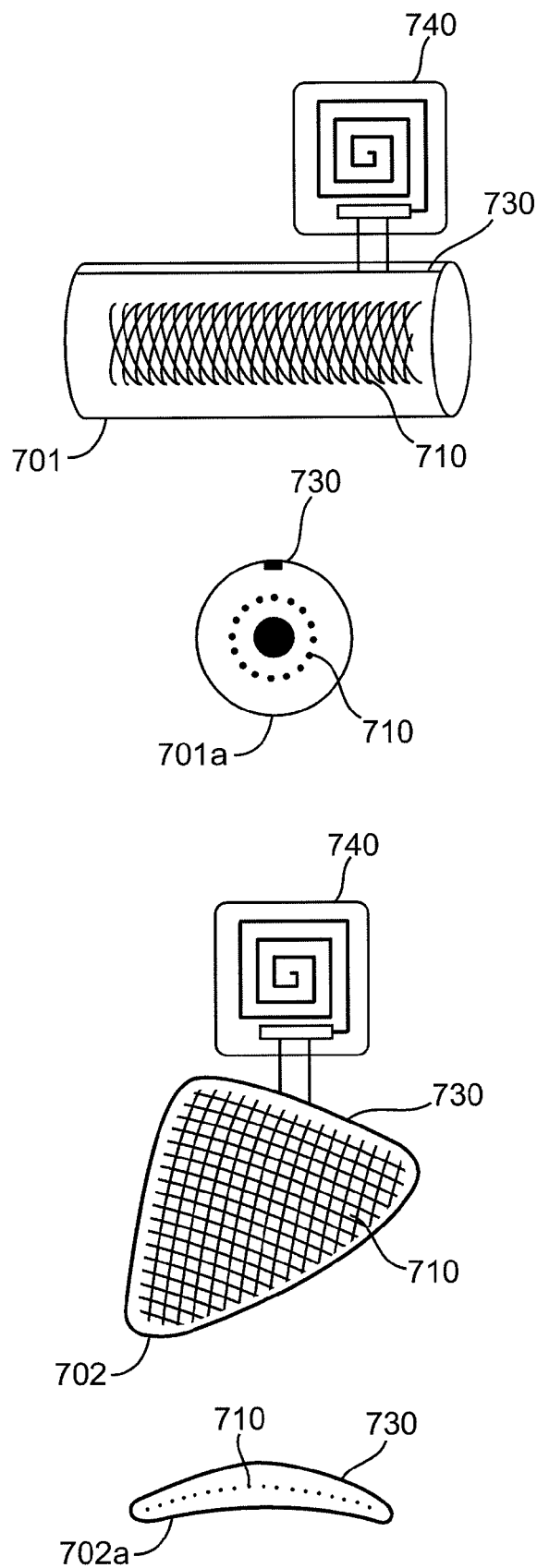

An exemplary reader module 120 is shown in FIG. 5 and includes LEDs to indicate normal or "on" function, failure, and emergency failure. An audible the alarm 126 could also be provided to alert with beeping sounds, or sensory, such as vibrations, or preferably a combination of any or all of the above. Optionally, the detector could have different auditory, visual, sensory, or different combinations to identify the source of the detected breach, especially with more than one chemical substance used. The alarm could further indicate the seriousness of the breach. For example, when breaches are detected, the volume of the alarm would increase to a higher level.

While the above is a complete description of the preferred embodiments of the invention, various alternatives, modifications, and equivalents may be used. Therefore, the above description should not be taken as limiting the scope of the invention which is defined by the appended claims.

What is claimed is:

1. An implantable prosthesis comprising:
    a wall having an exterior surface and an interior surface, and defining an internal compartment;
    a first electrical probe disposed on the exterior surface of the wall so that said first probe is exposed to an electrically conductive body fluid in an external environment when the device is implanted in a body;
    a second electrical probe embedded within the wall so that in the absence of a breach in the wall said second probe is electrically isolated both from the electrically conductive body fluids and from the internal compartment; and
    transponder circuitry, wherein the first electrical probe and the second electrical probe form a circuit in the transponder circuitry;
    wherein a partial or full breach in the external surface of the wall will allow intrusion of the electrically conductive body fluid into the wall to close or open said circuit in the transponder circuitry to provide an externally detectable signal.

2. A method for signaling wall breach of a prosthesis, said method comprising:
    inflating or filling an internal compartment of the prosthesis with a low electrical conductivity material;
    implanting the inflated or filled prosthesis in a body of a patient in the presence of an electrically conductive body fluid; and
    providing a first electrical probe on an exterior surface of a wall of the prosthesis in contact with the electrically conductive body fluid and a second electrical probe embedded within the wall such that said second probe remains electrically isolated both from the electrically conductive body fluid surrounding the exterior surface of the wall and from the internal compartment for so long as the wall remains unbreached;
    wherein a full or partial breach in the wall permits intrusion of the electrically conductive body fluid into an interior of the wall to electrically connect the first and second probes to close or open a circuit in a transponder to provide an externally detectable signal.

3. A method as in claim 2, wherein the prosthesis is a breast implant.

4. A method as in claim 2, wherein the prosthesis is a gastric balloon.

5. A method as in claim 2, wherein the prosthesis is a penile implant.

6. A method as in claim 2, further comprising directing an interrogation signal to an antenna of the transponder and detecting a return signal from the transponder, wherein the returned signal is altered, present or ceases only when the circuit has been closed or opened by the wall breach.

7. A method as in claim 2, wherein a partial exterior breach occurs and an inner surface of the prosthesis remains intact and no inflation or filling medium leaks from the prosthesis.

8. An implantable prosthesis as in claim 1, wherein the internal compartment comprises an inflatable compartment.

9. An implantable prosthesis as in claim 1, wherein the second electrical probe is embedded throughout the wall.

10. A method as in claim 2, wherein the prosthesis is inflated with a liquid or gel.

* * * * *